(12) United States Patent
Blom et al.

(10) Patent No.: US 7,987,851 B2
(45) Date of Patent: Aug. 2, 2011

(54) VALVED FENESTRATED TRACHEOTOMY TUBE HAVING OUTER AND INNER CANNULAE

(75) Inventors: Eric D. Blom, Carmel, IN (US); Bradley H. Quinn, Indianapolis, IN (US)

(73) Assignee: Hansa Medical Products, Inc., Indianapolis, IN (US)

( * ) Notice: Subject to any disclaimer, the term of this patent is extended or adjusted under 35 U.S.C. 154(b) by 558 days.

(21) Appl. No.: 11/318,649

(22) Filed: Dec. 27, 2005

(65) Prior Publication Data

US 2007/0144526 A1 Jun. 28, 2007

(51) Int. Cl.
*A62B 9/02* (2006.01)
*A62B 9/06* (2006.01)

(52) U.S. Cl. .............. 128/207.16; 128/207.14

(58) Field of Classification Search ............. 128/203.12, 128/207.16, 200.26, 207.14, 207.15, 200.24, 128/204.18, 205.24, 206.29, 207.12–207.13, 128/207.17–207.29

See application file for complete search history.

(56) References Cited

U.S. PATENT DOCUMENTS

| | | | |
|---|---|---|---|
| 1,598,283 A | 8/1926 | Kinney | |
| 2,892,458 A | 6/1959 | Auzin | |
| 3,688,774 A | 9/1972 | Akiyama | |
| 3,996,939 A | 12/1976 | Sheridan et al. | |
| 4,211,234 A | 7/1980 | Fisher | |
| 4,223,411 A | 9/1980 | Schoendorfer et al. | |
| 4,280,492 A | 7/1981 | Latham | |
| 4,304,228 A | 12/1981 | Depel | |
| 4,305,392 A | 12/1981 | Chester | |
| 4,315,505 A * | 2/1982 | Crandall et al. | 128/200.26 |
| 4,327,721 A | 5/1982 | Goldin et al. | |
| 4,449,523 A | 5/1984 | Szachowicz et al. | |
| 4,459,984 A * | 7/1984 | Liegner | 128/207.15 |
| 4,469,100 A * | 9/1984 | Hardwick | 606/127 |
| 4,573,460 A | 3/1986 | Szachowicz | |
| 4,584,998 A | 4/1986 | McGrail | |
| 4,589,410 A | 5/1986 | Miller | |
| 4,596,248 A | 6/1986 | Lieberman | |
| 4,607,635 A | 8/1986 | Heyden | |
| 4,627,433 A * | 12/1986 | Lieberman | 128/207.16 |
| 4,632,108 A | 12/1986 | Geil | |

(Continued)

FOREIGN PATENT DOCUMENTS

DE 34 06 294 A1 9/1985

(Continued)

OTHER PUBLICATIONS

European search report from EP 06 02 0526 dated Apr. 10, 2007.

(Continued)

*Primary Examiner* — Justine Yu
*Assistant Examiner* — Rachel Young
(74) *Attorney, Agent, or Firm* — Barnes & Thornburg LLP

(57) ABSTRACT

A tracheotomy tube apparatus includes an outer cannula having first and second ends, a fenestration along the length of the outer cannula between the first and second ends, and a first inner cannula sized for insertion into the outer cannula. The first inner cannula includes a resilient region which lies adjacent the fenestration when the first inner cannula is properly oriented within the outer cannula, and a valve operatively associated with the first inner cannula. A region between the resilient region and the valve provides a passageway between the first inner cannula and the outer cannula when the first inner cannula is properly oriented within the outer cannula.

21 Claims, 8 Drawing Sheets

U.S. PATENT DOCUMENTS

| | | |
|---|---|---|
| 4,637,389 A | 1/1987 | Heyden |
| 4,762,125 A | 8/1988 | Leiman et al. |
| 4,834,087 A | 5/1989 | Coleman et al. |
| 4,840,173 A | 6/1989 | Porter, III |
| 4,852,565 A * | 8/1989 | Eisele ................ 128/207.14 |
| 5,056,515 A | 10/1991 | Abel |
| 5,067,497 A | 11/1991 | Greear et al. |
| 5,107,828 A | 4/1992 | Koss et al. |
| 5,123,922 A * | 6/1992 | Berg ........................... 623/9 |
| 5,201,310 A | 4/1993 | Turnbull |
| 5,217,008 A | 6/1993 | Lindholm |
| 5,255,676 A | 10/1993 | Russo |
| 5,297,546 A | 3/1994 | Spofford et al. |
| 5,329,921 A | 7/1994 | Socaris et al. |
| 5,339,808 A | 8/1994 | Don Michael |
| 5,343,857 A | 9/1994 | Schneider et al. |
| 5,349,950 A | 9/1994 | Ulrich et al. |
| 5,391,205 A | 2/1995 | Knight |
| 5,392,775 A | 2/1995 | Adkins, Jr. et al. |
| 5,458,139 A | 10/1995 | Pearl |
| 5,497,768 A | 3/1996 | Lomholt |
| 5,507,279 A | 4/1996 | Fortune et al. |
| 5,515,844 A | 5/1996 | Christopher |
| 5,584,288 A | 12/1996 | Baldwin |
| 5,599,333 A | 2/1997 | Atkinson |
| RE35,595 E | 8/1997 | Six |
| 5,687,767 A | 11/1997 | Bowers |
| 5,688,256 A | 11/1997 | Surratt et al. |
| 5,746,199 A | 5/1998 | Bayron et al. |
| 5,771,888 A | 6/1998 | Keim |
| 5,957,978 A * | 9/1999 | Blom .............................. 623/9 |
| 6,053,167 A | 4/2000 | Waldeck |
| 6,089,225 A | 7/2000 | Brown et al. |
| 6,102,038 A | 8/2000 | DeVries |
| 6,105,577 A | 8/2000 | Varner |
| 6,135,110 A * | 10/2000 | Roy ........................ 128/207.15 |
| 6,135,111 A | 10/2000 | Mongeon |
| 6,463,927 B1 | 10/2002 | Pagan |
| 6,722,367 B1 | 4/2004 | Blom |
| 6,814,077 B1 * | 11/2004 | Eistert ..................... 128/207.15 |
| 2003/0084905 A1 * | 5/2003 | Ortiz ........................ 128/207.29 |
| 2004/0123868 A1 * | 7/2004 | Rutter ..................... 128/207.14 |

FOREIGN PATENT DOCUMENTS

| | | |
|---|---|---|
| DE | 37 20 482 A1 | 12/1988 |
| DE | 38 13 705 A1 | 1/1989 |
| DE | 195 13 831 C1 | 5/1996 |
| DE | 101 09 935 A1 | 11/2001 |
| WO | WO 99/07428 | 2/1999 |
| WO | WO 99/12599 | 3/1999 |
| WO | WO 00/32262 | 6/2000 |

OTHER PUBLICATIONS

Quick Reference Guide to Shiley's "Quality-Of Life" Line of Tracheostomy Products, 1991.

Granuloma Associated with Fenestrated Tracheostomy Tubes, Padmanabhan Siddharth, MD, PhD, FACS and Lawrence Mazzarella, MD, FACS, Case Reports, vol. 150, Aug. 1985, pp. 279-280.

D. Hessler, MD, K. Rehder, MD and S.W. Karveth, MD, "Tracheostomy Cannula for Speaking During Artificial Respiration", Anesthesiology, vol. 25, No. 5, pp. 719-721 (1964).

* cited by examiner

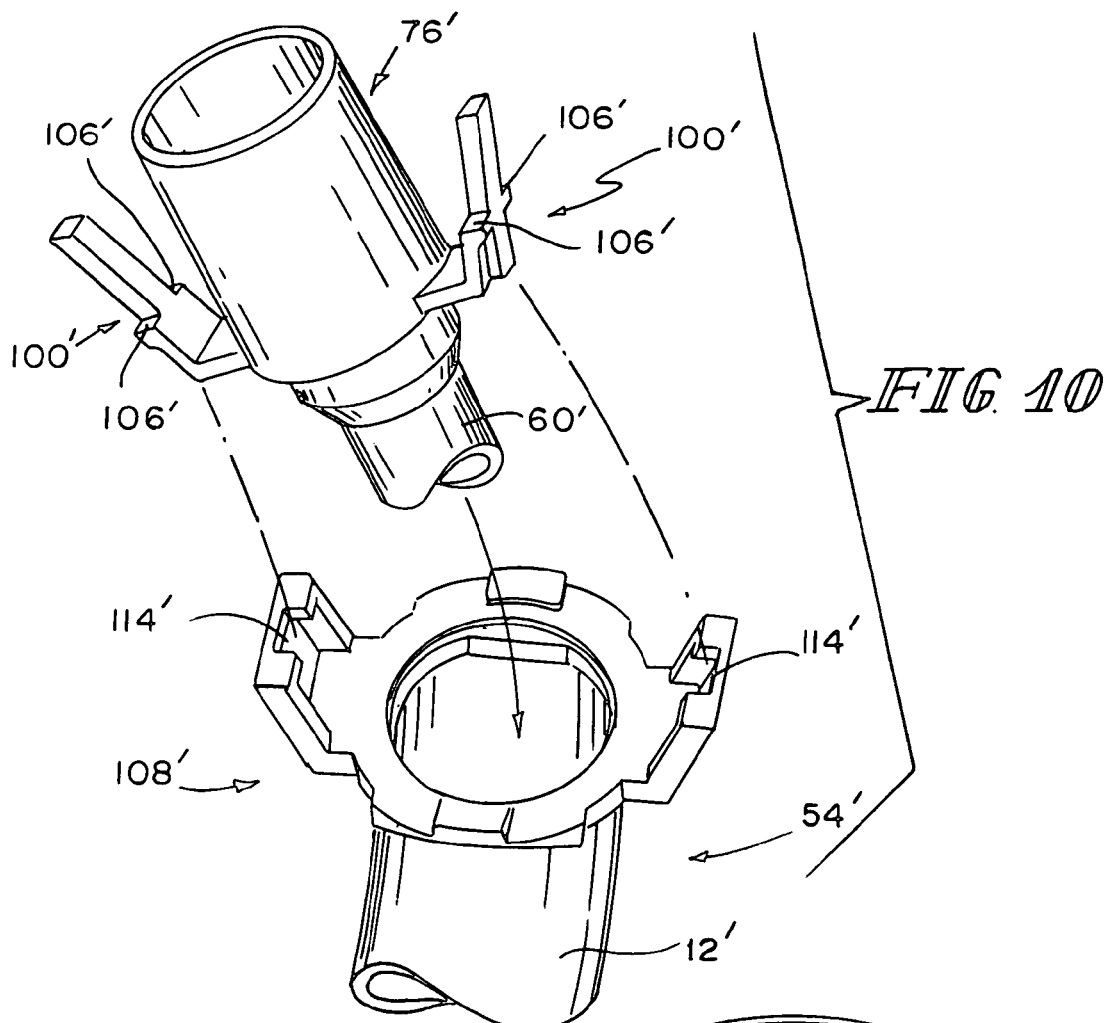
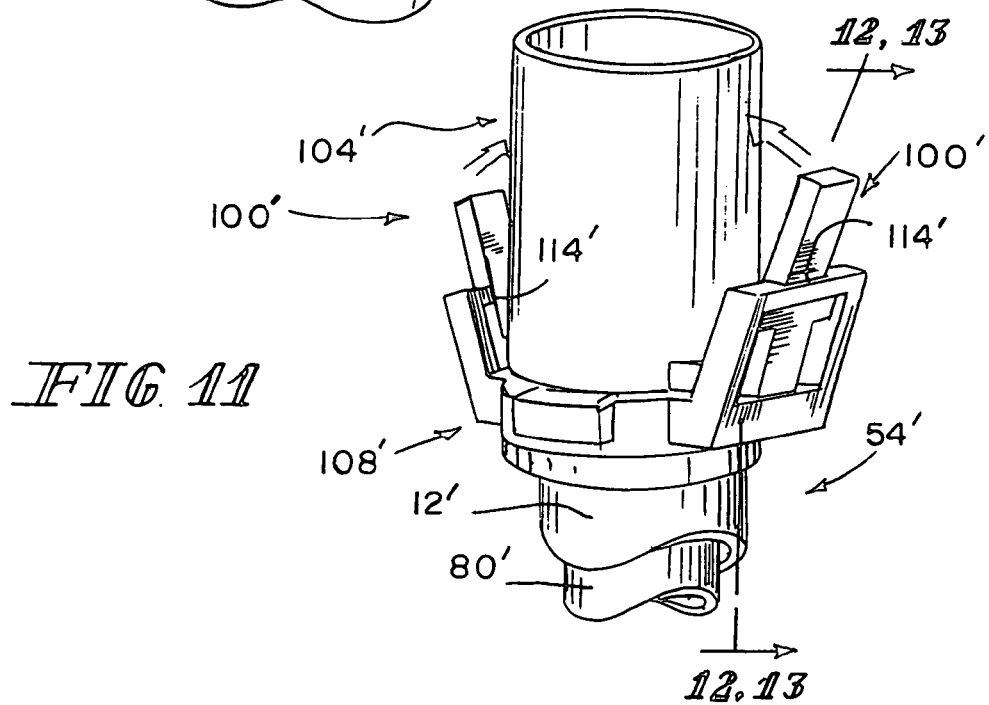

VALVED FENESTRATED TRACHEOTOMY TUBE HAVING OUTER AND INNER CANNULAE

FIELD OF THE INVENTION

This invention relates to improvements in tracheotomy tubes.

BACKGROUND OF THE INVENTION

This invention is directed toward the problem of being unable to produce audible laryngeal voice, and thus, the inability to speak, that confronts individuals whose breathing is provided mechanically by a respirator which is connected to a cuffed tracheotomy tube inserted into the trachea of a wearer below the level of the vocal cords. The cuff on the tracheotomy tube is inflated, for example, with air, so that the cuff seals substantially fluid tight against the wall of the trachea. The purposes of the inflated cuff include: to protect against leakage of saliva and other secretions around the tracheotomy tube and into the lungs; and, to prevent the air being delivered under pressure from the respirator through the tracheotomy tube to the lungs and exhalation from the lungs from escaping around the tracheotomy tube and out through the mouth and nose of the wearer. In other words, the inflated cuff provides a closed mechanical respiratory system that completely bypasses the upper airway above the level of the tracheotomy tube, including the vocal cords. The side effects of this include the elimination of exhaled airflow upward through the vocal cords. Of course, this eliminates voice production by exhalation products from the lungs.

Currently, there are three available options for individuals being mechanically ventilated via a cuffed tracheotomy tube to produce audible voice and speech with their own vocal cords. The first of these options is described in O. Hessler, M. D., K. Rehder, M. D., and S. W. Karveth, M C, U.S.A., "Tracheostomy Cannula for Speaking During Artificial Respiration," Anesthesiology, vol. 25, no. 5, pp. 719-721 (1964). There is no known commercially available device constructed as described in Hessler, et al.

The second option is a so-called "talking tracheotomy tube," which is a conventional cuffed tracheotomy tube manufactured with an 8-10 French conduit extending along its length. The distal end of this conduit terminates above the level of the inflated cuff. The proximal end of this conduit is connected to a source of, for example, compressed air. Examples of such a device are manufactured by Sims Portex, Inc., and Bivona Surgical Inc. The wearer of such a device is able to stop and start the flow of compressed air to the distal end of this conduit, thereby enabling the stopping and starting of the flow of air upward through his or her vocal cords, enabling the wearer to produce speech. This speech airflow is completely independent of the respiratory airflow through the tracheotomy tube. Such talking tracheotomy tubes have been available for several years, but are not in widespread use, perhaps owing to numerous mechanical limitations.

The third option is the system illustrated and described in U.S. Pat. No. 6,722,367, the disclosure of which is hereby incorporated herein by reference.

The following are also of interest: U.S. Pat. Nos. 3,688,774; 3,996,939; 4,211,234; 4,223,411; 4,280,492; 4,304,228; 4,449,523; 4,459,984; 4,573,460; 4,589,410; 4,596,248; 4,852,565; 5,056,515; 5,107,828; 5,217,008; 5,255,676; 5,297,546; 5,329,921; 5,339,808; 5,343,857; 5,349,950; 5,391,205; 5,392,775; 5,458,139; 5,497,768; 5,507,279; 5,515,844; 5,584,288; 5,599,333; RE35,595; 5,687,767; 5,688,256; 5,746,199; 5,771,888; 5,957,978; 6,053,167; 6,089,225; 6,102,038; 6,105,577; 6,135,111; 6,463,927; 6,814,007; foreign/international patent publications: DE 25 05 123; DE 37 20 482; DE 38 13 705; DE 195 13 831; WO 99/07428; WO 99/12599; WO 00/32262; other publications: Quick Reference Guide to Shiley's "Quality-Of Life" Line of Tracheostomy Products, 1991; Granuloma Associated with Fenestrated Tracheostomy Tubes, Padmanabhan Siddharth, MD, PhD, FACS and Lawrence Mazzarella, MD, FACS, Case Reports, vol. 150, August 1985, pp. 279-280; Technical Support Information Connections with the Passy-Muir Tracheostomy and Ventilator Speaking Valves, one sheet; Tracheostomy and Laryngectomy Tubes, pp. 568 and 572; Tracheostomy Tube Adult Home Care Guide, Shiley Tracheostomy Products, Mallinckrodt Medical pp. 1-40; D. Hessler, MD, K. Rehder, MD and S. W. Karveth, MD, "Tracheostomy Cannula for Speaking During Artificial Respiration", Anesthesiology, vol. 25, No. 5, pp. 719-721 (1964). No representation is intended by this listing that a thorough search of all material prior art has been conducted, or that no better art than that listed is available. Nor should any such representation be inferred. The disclosures of all of the above are hereby incorporated herein by reference.

A ventilator-dependent patient breathing through a cuffed tracheotomy tube is unable to produce audible voice with his or her vocal cords because the cuff of the tracheotomy tube he or she wears prevents exhalations from going around the lower end of the tube and upward through the vocal cords. This situation continues until the wearer's condition improves sufficiently that the cuff on the tracheotomy tube can be deflated so that exhaled air can pass around the tracheotomy tube and up through the wearer's vocal cords, mouth and nose, permitting audible vocal cord vibrations for speech.

The invention alleviates this situation. When coupled to a respirator with its cuff inflated, a valved, cuffed tracheotomy tube system according to the invention directs air on the inhalation cycle of the respirator to the lungs. Exhalations are directed by the valved, cuffed tracheotomy tube system according to the invention to the upper airway, permitting vocal cord vibration and audible laryngeal speech.

SUMMARY OF THE INVENTION

According to an aspect of the invention, a tracheotomy tube apparatus includes an outer cannula having first and second ends and a fenestration along the length of the outer cannula between the first and second ends. The apparatus further includes a first inner cannula sized for insertion into the outer cannula. The first inner cannula has a raised region on an outer sidewall thereof substantially to close the fenestration when the first inner cannula is inserted into the outer cannula.

Illustratively according to this aspect of the invention, the apparatus further comprises a second inner cannula for insertion into the outer cannula when the first inner cannula is removed therefrom. The second inner cannula includes a resilient region which lies adjacent the fenestration when the second inner cannula is properly oriented within the outer cannula. The second inner cannula further includes a valve operatively associated with the second inner cannula and a region between the resilient region and the end thereof which provides a passageway between the second inner cannula and the outer cannula when the second inner cannula is properly oriented within the outer cannula.

According to another aspect of the invention, a tracheotomy tube apparatus includes an outer cannula having first and second ends and a fenestration along the length of the outer cannula between the first and second ends. The apparatus further includes an inner cannula sized for insertion into the outer cannula. The inner cannula includes a resilient region which lies adjacent the fenestration when the inner cannula is properly oriented within the outer cannula. The inner cannula further includes a valve operatively associated with the inner cannula and a region between the resilient region and the valve which provides a passageway between the inner cannula and the outer cannula when the inner cannula is properly oriented within the outer cannula.

According to another aspect of the invention, a tracheotomy tube apparatus includes an outer cannula and an inner cannula sized for insertion into the outer cannula. A first coupler is provided on an outer end of the outer cannula. A second coupler is provided on an outer end of the inner cannula. One of the first and second couplers is provided with at least one surface for guiding the inner cannula into a predetermined orientation with respect to the outer cannula when the inner cannula is inserted into the outer cannula. The other of the first and second couplers is provided with a cooperating surface for cooperating with the at least one surface for guiding the inner cannula into the predetermined orientation with respect to the outer cannula.

According to another aspect of the invention, a tracheotomy tube comprises an inflatable cuff formed by a sleeve including a first end, a second end, and a third region between the first and second ends. The sleeve is located around the tracheotomy tube with at least the first end of the sleeve between the tracheotomy tube and the third region of the sleeve. A conduit extends from a first end of the tracheotomy tube to the cuff for introducing an inflating fluid into the cuff when it is desired to inflate the cuff and removing inflating fluid from the cuff when it is desired to deflate the cuff.

According to another aspect of the invention, a tracheotomy tube apparatus includes an outer cannula having first and second ends and a fenestration along the length of the outer cannula between the first and second ends. The apparatus further includes an inflatable cuff formed on the outer cannula between the fenestration and the second end. A first conduit extends from the first end to the cuff for introducing an inflating fluid into the cuff when it is desired to inflate the cuff and removing inflating fluid from the cuff when it is desired to deflate the cuff. The apparatus further includes an inner cannula sized for insertion into the outer cannula. The inner cannula includes a second conduit to evacuate a region of a trachea of a wearer adjacent the cuff. The second conduit includes an opening which lies adjacent the closest point in the fenestration to the cuff when the inner cannula is in a use orientation in the outer cannula.

According to another aspect of the invention, a tracheotomy tube apparatus includes an outer cannula and an inner cannula sized for insertion into the outer cannula. At least one tab is provided on an outer end of one of the outer cannula and the inner cannula. The at least one tab includes an engaging surface. At least one coupler is provided on an outer end of the other one of the outer cannula and the inner cannula for engagement by the at least one tab. The at least one coupler includes a portion for cooperating with the engaging surface and a notch for receiving a portion of the at least one tab for orienting the inner cannula in a predetermined orientation with respect to the outer cannula.

Illustratively according to this aspect of the invention, the at least one tab is flexibly formed or mounted to said one of the outer cannula and the inner cannula.

According to another aspect of the invention, a tracheotomy tube comprises an inflatable cuff, a conduit extending from a first end of the tracheotomy tube to the cuff for introducing an inflating fluid into the cuff when it is desired to inflate the cuff and removing inflating fluid from the cuff when it is desired to deflate the cuff, and at least one fenestration through a sidewall of the tracheotomy tube to permit the flow of gas from inside the tracheotomy tube through the at least one fenestration and out of the tracheotomy tube. The at least one fenestration is immediately adjacent the cuff.

BRIEF DESCRIPTION OF THE DRAWINGS

The invention may best be understood by referring to the following detailed description and accompanying drawings which illustrate the invention. In the drawings.

DETAILED DESCRIPTIONS OF ILLUSTRATIVE EMBODIMENTS

Figure 1:
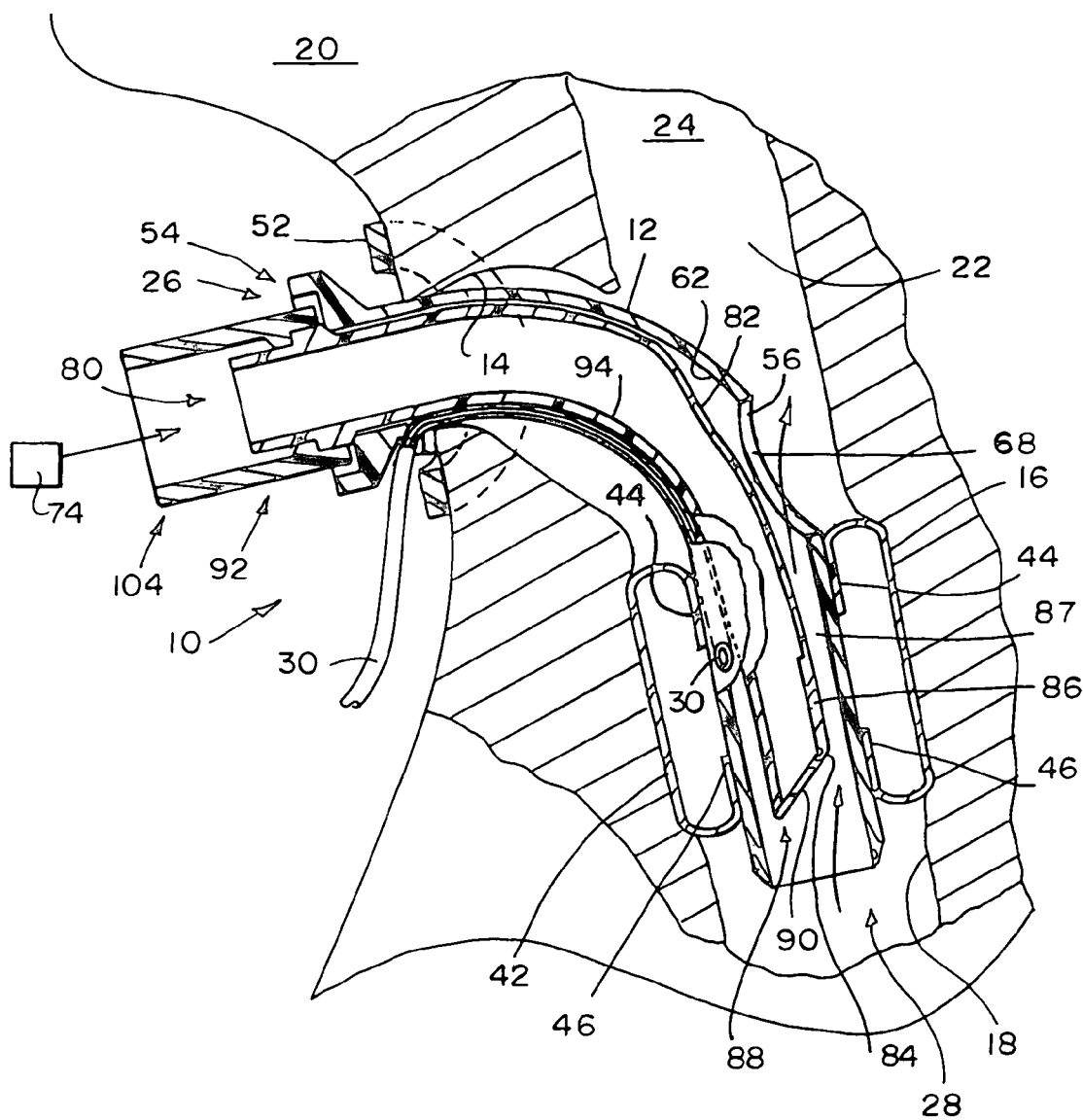
FIG. 1 illustrates a partly fragmentary lateral section through the trachea, tracheostoma and lower pharynx of a wearer fitted with a device according to the present invention.
Figures 2, 2A:
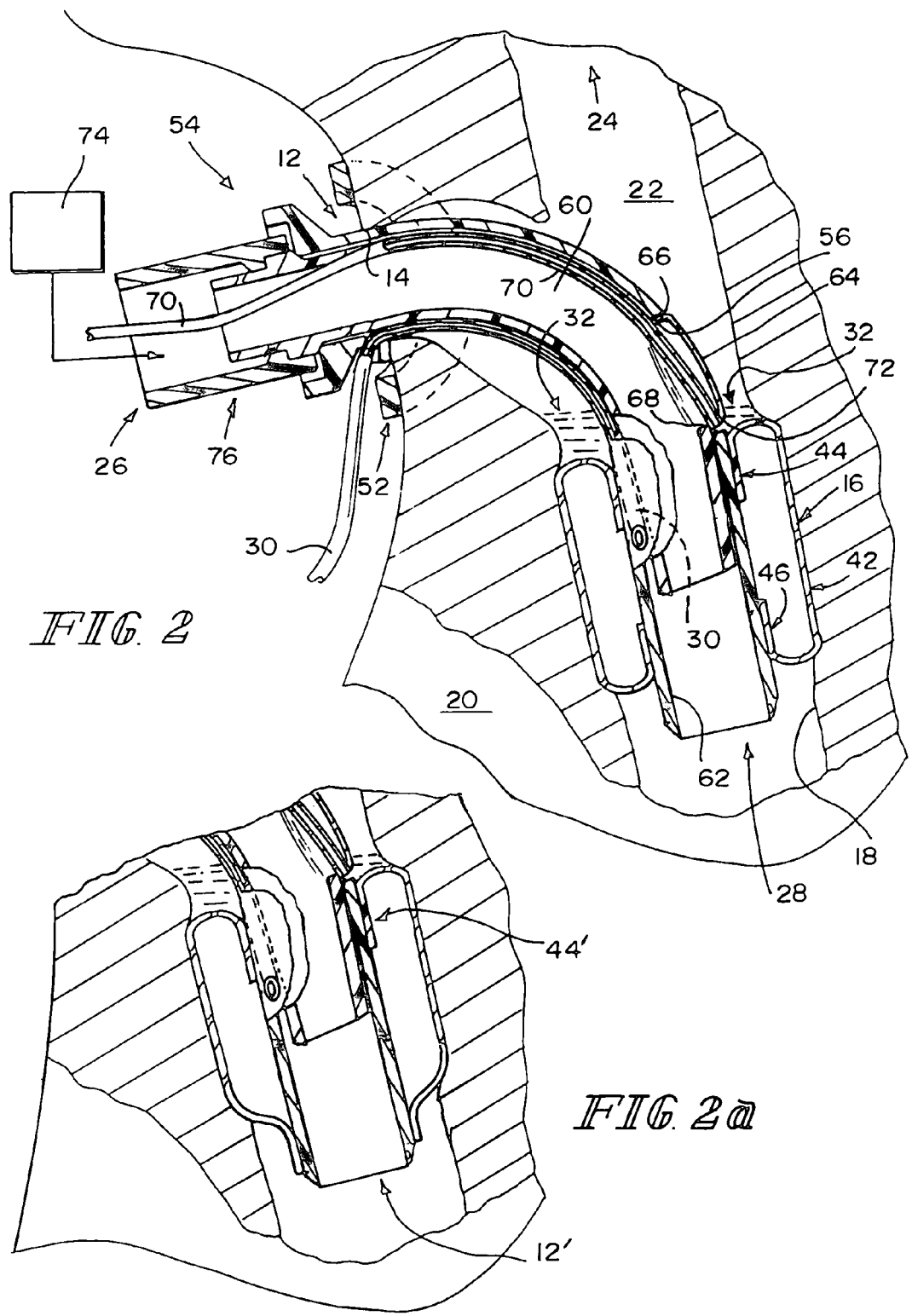
FIG. 2 illustrates a partly fragmentary lateral section through the trachea, tracheostoma and lower pharynx of a wearer fitted with a device according to the present invention.
FIG. 2a illustrates an alternative detail to a detail of the device illustrated in FIG. 2.

Referring now particularly to FIGS. 1 and 2, a speaking tracheotomy tube system 10 includes an outer cannula 12 for insertion into a tracheostoma 14. Outer cannula 12 includes an inflatable cuff 16. Cuff 16 lies in the trachea 18 of a wearer 20 below the passageway 22 upward into the pharynx 24 of the wearer 20. Outer cannula 12 also includes a first port 26 which resides outside the neck of the wearer 20 during use and a second port 28 which resides inside the neck of the wearer 20 below cuff 16 during use. The cuff 16 is inflatable through a line 30 once the outer cannula 12 is in place in the trachea 18 to minimize the passage of secretions 32 from the upper respiratory tract, including pharynx 24, downward into the lungs of the wearer 20. Such secretions 32 pool above the cuff 16 when the cuff 16 is inflated in place. The construction of the cuff 16 as a sleeve 42 with its upper and lower ends 44, 46, respectively, tucked under, rather than extending beyond the cuff 16 up and down the outer sidewall of the outer cannula 12, is aided by the use of thin-walled material for the cuff 16. In an alternative embodiment, illustrated in FIG. 2a, only upper end 44' is tucked under, rather than extending beyond the cuff 16 up the outer sidewall of the outer cannula 12'. The constructions illustrated in FIGS. 2 and 2a provide certain benefits which will be discussed subsequently.

The outer cannula 12 includes a pivotally mounted attachment plate 52 adjacent its proximal end 54 to facilitate attachment, for example, by a strap or belt around the neck of the wearer 20. The outer cannula 12 also includes a fenestration 56 which permits the wearer 20 to speak by providing a flow of exhaled respiratory gases upward through the fenestration 56 and into the pharynx 24 in a manner which will be described. Speech may then be articulated in accordance with known principles. Although only one such fenestration 56 is illustrated, it should be understood that any number of fenestrations 56 may be provided in the outer cannula 12 for this purpose. The construction of cuff 16, with its doubled-over upper and lower ends 44, 46, respectively, (FIG. 2) or doubled-over upper end 44' (FIG. 2a), permits location of the fenestration(s) 56 lower on the outer cannula 12. The proximity of the cuff 16 to the fenestration(s) 56 locates the site from which respiratory products are released through outer cannula 12 lower in the trachea 18, which is thought to aid in the production of speech. Additionally, the proximity of the cuff 16 to fenestration(s) 56 provides some additional protection of the tissue of the trachea 18 against abrasive contact with the edges of the fenestration(s) 56 by virtue of the stand-off provided by the inflated cuff 16. Such contact is known to promote the growth of granulation tissue at the site of such contact, which is to be avoided. This same standoff also increases clearance between the fenestration(s) 56 and the wall of the trachea 18. This reduces the likelihood that the flow of respiration products from fenestration(s) 56 upward through the pharynx 24 will be blocked by the wall of the trachea 18. Among other benefits of this more distal positioning of the cuff 16 are that it increases the likelihood that the fenestration(s) 56 will remain operatively in the trachea 18 if the wearer 20 has an anatomically thick neck, or if the ventilator tubing to which the outer cannula 12, 12' is routinely coupled should pull at the outer cannula 12, 12', causing it to work outward from the tracheostoma 14, or where the wearer 20's tracheal lumen is anatomically narrow. These are not uncommon occurrences among wearers of tracheotomy tubes. Typical prior art cannulae exhibit the following spacings between the bottom of the fenestration and the top of the cuff: 0.285" (about 7.2 mm); 0.345" (about 8.8 mm); 0.375" (about 9.5 mm); and, 0.41" (about 10.4 mm). This spacing is necessary to provide the upper attachment of the prior art cuff to the outer sidewall of the prior art cannula. This distance can be reduced effectively to zero with the configurations of the present invention, but in any event less than the 0.285" (about 7.2 mm) minimum achieved with the prior art cannulae identified above.

Figure 3:
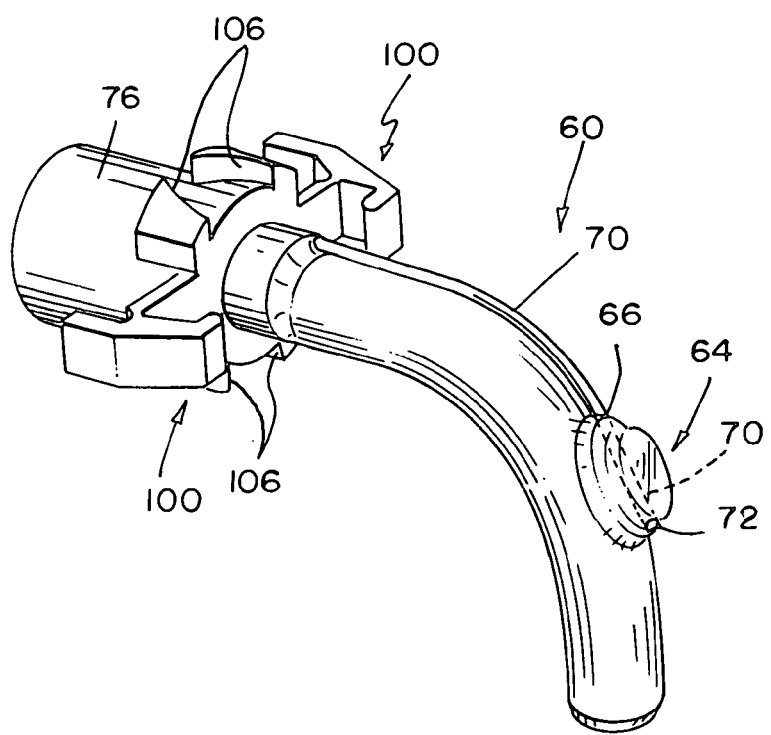
FIGS. 3-4 illustrate a perspective view and a fragmentary elevational view of certain details of the device illustrated in FIG. 2.
Figure 4:
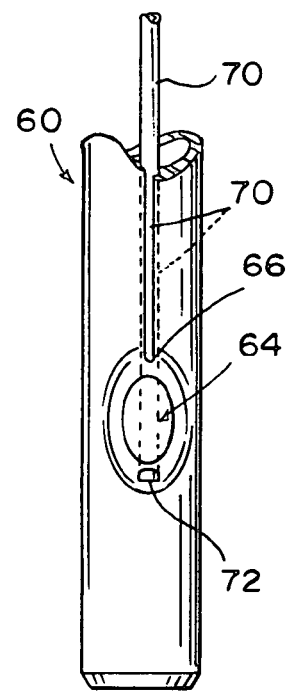

Referring now particularly to FIGS. 2-4, during extended periods when the wearer 20 is not going to be speaking, for example, when the wearer is asleep, an inner cannula 60 is inserted into the lumen 62 of the outer cannula 12, 12'. Inner cannula 60 includes a raised region 64 on its outer sidewall at the level of fenestration 56. The region 64 includes a sidewall 66 that extends into relatively close proximity with the sidewall 68 of fenestration 56 to fill fenestration 56 relatively completely when inner cannula 60 is in place in lumen 62. This also protects the trachea 18 of the wearer 20 against irritation by the relatively sharp edge of the sidewall 68 of fenestration 56, reducing irritation of the tissue of the trachea 18 and the resultant tendency for granulation tissue to form in the region of the fenestration 56. To evacuate pooling secretions 32, a tube 70 extends down the sidewall of inner cannula 60. Tube 70 terminates at an open end 72 at the bottommost extent of fenestration 56 to expose the secretions 32 to suction at open end 72 of tube 70. Owing to the construction of cuff 16 with its doubled-under end 44, this location generally coincides with the top of the cuff 16 at the bottommost extent of fenestration 56. Owing to this construction, extraction of secretions 32 is somewhat more predicable and complete.

In addition, it is contemplated that replacement of the inner cannula 60 may occur more frequently and with less difficulty and potential trauma than outer cannula 12, 12', which is typically placed in the trachea for a longer term. The outer cannula 12, 12' also is typically constructed from more rigid, durable materials. The inner cannula 60, on the other hand, is typically constructed from somewhat more pliable, resilient materials. Notably, the inner cannula 60 must be constructed from material which is sufficiently resilient for the region 64 to snap into and out of engagement in the fenestration 56 without causing undue discomfort to the wearer 20. Typically, both the outer 12, 12' and inner cannulae 60 are constructed from suitable filled and/or unfilled resin(s) and/or polymer(s). Inner cannula 60 typically can be relatively straightforwardly replaced by disconnecting it from the ventilator 74 (illustrated diagrammatically) to which the outer end 76 of inner cannula 60 is attached in use and withdrawing inner cannula 60 from outer cannula 12, 12'. Because of the relative ease with which inner cannula 60 can be removed and replaced with a fresh cannula 60 having a fresh tube 70, providing tube 70 on inner cannula 60 rather than on outer cannula 12, 12' affords somewhat more reliable patency of tube 70 than if the tube 70 were to be provided in outer cannula 12, 12' which is not so readily removed for cleaning or replacement.

Referring again to FIG. 1, during times when the wearer desires to speak, such as during therapy, when visitors are in the wearer's room, and so on, inner cannula 60 is removed from outer cannula 12, 12' and replaced with a speaking inner cannula 80. Speaking inner cannula 80 includes a flexible, balloon-like region 82 adjacent fenestration 56, a region 86 between region 82 and lower end 84 which provides a passageway 87 between region 86 and the inner sidewall of lumen 62 of outer cannula 12, 12', and a valve 88 including a resilient flap 90 at its lower end 84. Speaking inner cannula 80 functions in the following manner when it is inserted into outer cannula 12, 12', locked in place and its outer end 92 attached to ventilator 74. During pressurization by the ventilator 74, balloon-like region 82 inflates, sealing against fenestration 56 and preventing the escape of ventilator-provided air upward through fenestration 56 and the wearer 20's pharynx 24. Flap 90 of valve 88 opens, permitting air to flow into the lungs of the wearer 20. During exhalation, the ventilator 74 removes pressure at the outer end 92 of speaking inner cannula 80. The flap 90 of valve 88 closes, closing the lumen 94 of speaking inner cannula 80 against the passage upward of respiratory products through speaking inner cannula 80, permitting the balloon-like region 82 to deflate somewhat and opening passageway 87 upward from the lungs of the wearer 20 through fenestration 56. Respiratory products in the wearer 20's lungs escape upward through passageway 87, through fenestration 56, and are released into the wearer's pharynx 24, providing sufficient flow to permit the wearer 20 to speak.

Figure 5:
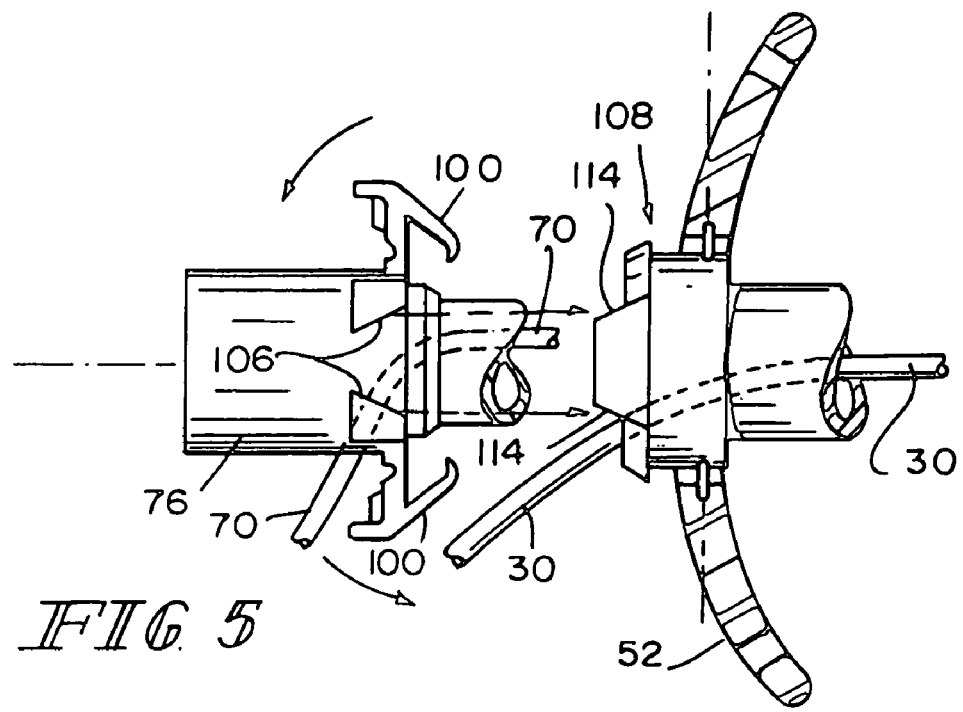
FIGS. 5-6 illustrate fragmentary, partly sectional elevational views of the device illustrated in FIGS. 2-4.
Figure 6:
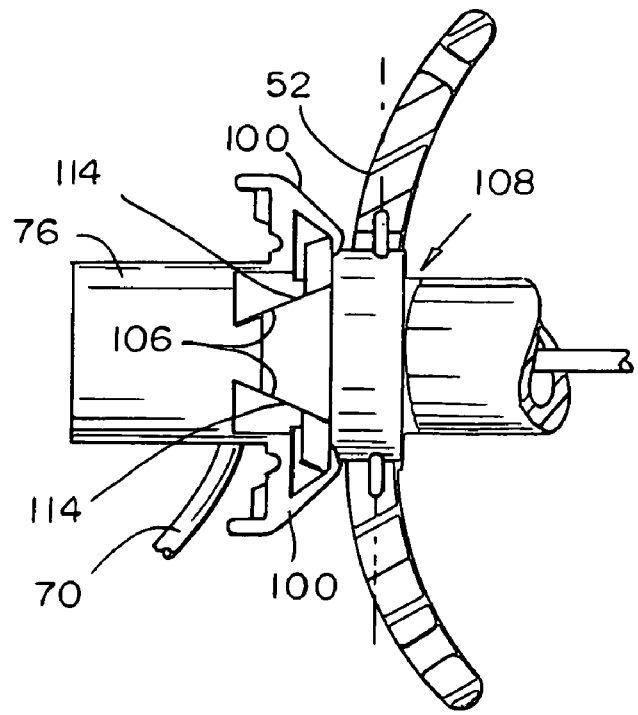

Referring now to FIGS. 3, 5 and 6, the inner cannula 60 and speaking inner cannula 80 are releasably fixed to the outer cannula 12 by one or more (two in the illustrated embodiment) locking tabs 100 which may be formed with, and from the same material as, the couplers 76, 104 of cannulae 60, 80 by which cannulae 60, 80 are coupled to ventilator 74. The tabs 100 are flexibly formed or mounted to the couplers 76, 104 of inner cannulae 60, 80. The couplers 76, 104 also are provided with beveled surfaces 106. A coupler 108 is provided at the proximal end 54 of outer cannula 12. The coupler 108 includes beveled surfaces 114 complementarily beveled to surfaces 106 to aid in guiding raised region 64 of inner cannula 60 and the balloon-like region 82 of speaking inner cannula 80 into the appropriate orientations to orient the raised region 64 of inner cannula 60 and the balloon-like region 82 of speaking inner cannula 80 to cooperate with fenestration(s) 56 when inner cannula 60 and speaking inner cannula 80, respectively, are inserted into outer cannula 12. While the illustrated complementary surfaces 106 and 114 are flat and angled toward each other, it should be understood that other complementary surfaces could be provided on the couplers 108 and 76, 104. For example, these surfaces could be generally part right circular cylindrical, part spherical, conical, frustoconical, and so on, as long as they effect the appropriate orientation of raised region 64 of inner cannula 60 and the balloon-like region 82 of speaking inner cannula 80 with respect to fenestration(s) 56 when inner cannula 60 and speaking inner cannula 80, respectively, are inserted into outer cannula 56.

An alternative coupling mechanism is illustrated in FIGS. 10-13. Referring to FIGS. 10-13, an inner cannula 60' (FIG. 10) and speaking inner cannula 80' (FIGS. 11-13) are releasably fixed to an outer cannula 12' by one or more (two in the illustrated embodiment) locking tabs 100' which may be formed with, and from the same material as, the couplers 76', 104' of cannulae 60', 80' by which cannulae 60', 80' are coupled to the ventilator (not shown in FIGS. 10-13). The tabs 100' are flexibly formed or mounted to the couplers 76', 104' of inner cannulae 60', 80'. The tabs 100' are provided with engaging surfaces 106'. A coupler 108' is provided at the proximal end 54' of outer cannula 12'. The coupler 108' includes a notch 114' for receiving the portion of each tab 100' which extends beyond engaging surfaces 106' and portions 116 for capturing engaging surfaces 106'. This configuration also promotes correct orientation of the raised region (not shown in FIGS. 10-13) of inner cannula 60' and the balloon-like region (not shown in FIGS. 10-13) of speaking inner cannula 80' with the fenestration (not shown in FIGS. 10-13) of outer cannula 12' when inner cannula 60' and speaking inner cannula 80', respectively, are inserted into outer cannula 12'.

Figure 7:
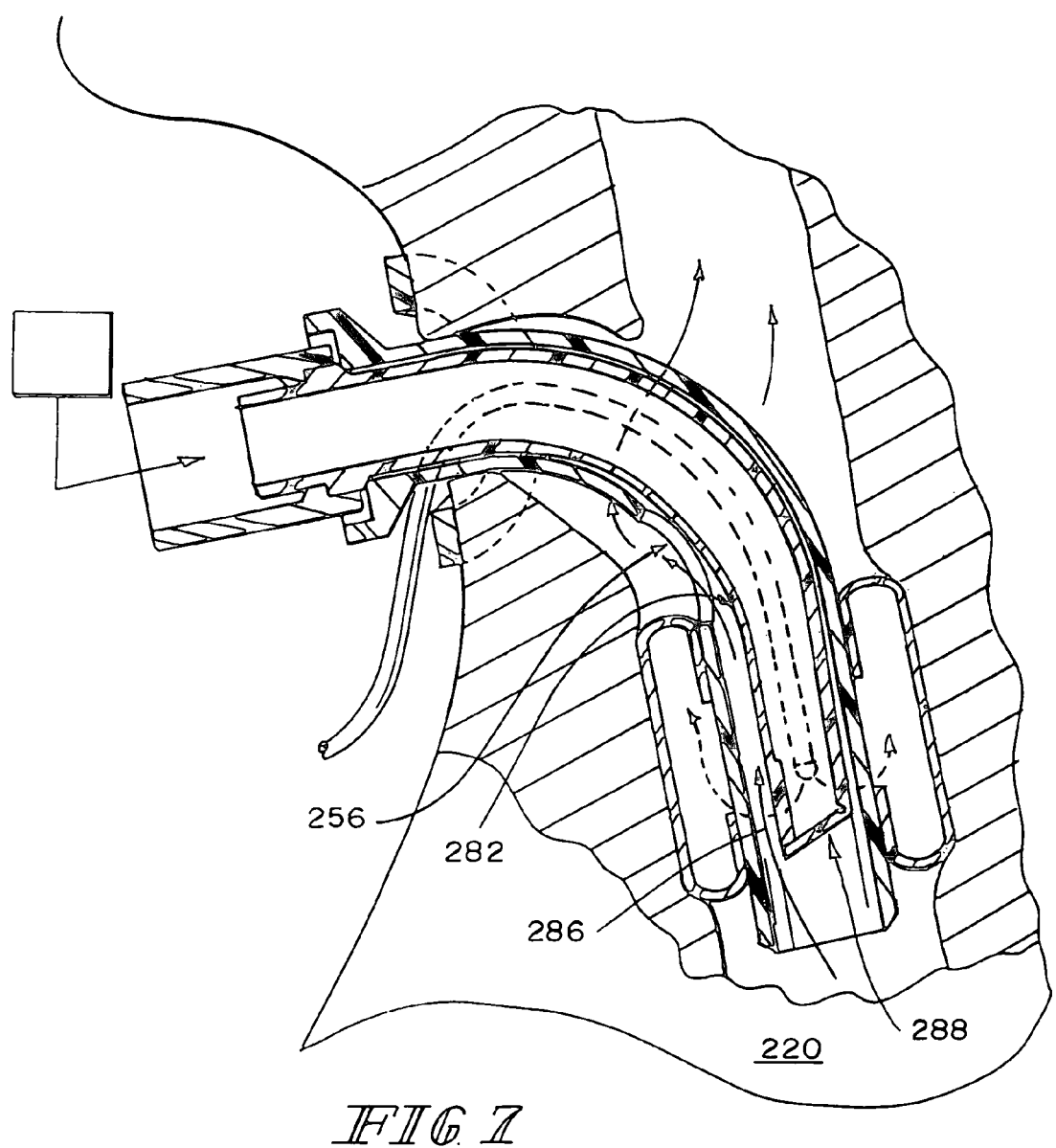
FIG. 7 illustrates a partly fragmentary lateral section through the trachea, tracheostoma and lower pharynx of a wearer fitted with a device according to the present invention.
Figure 8:
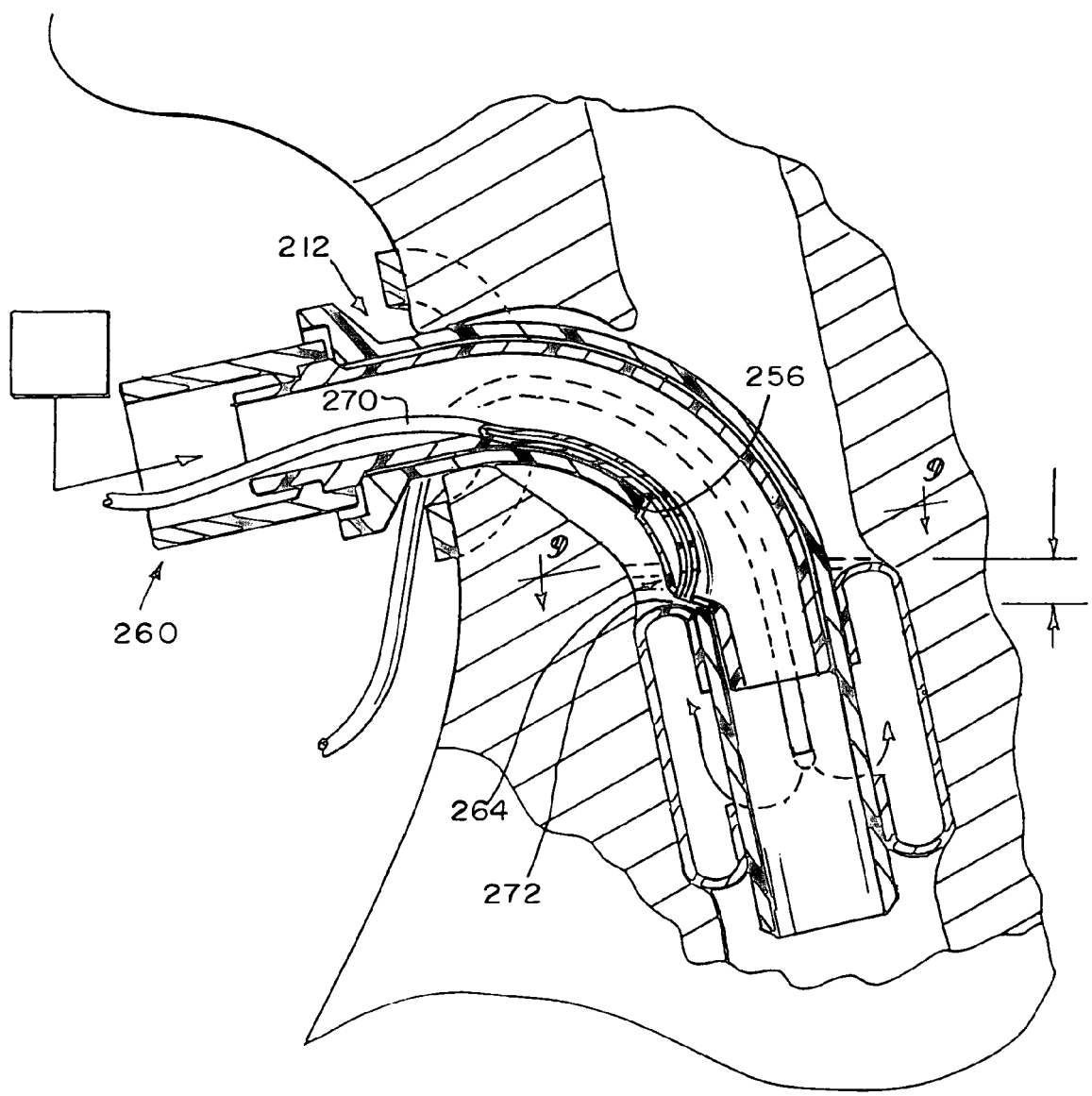
FIG. 8 illustrates a partly fragmentary lateral section through the trachea, tracheostoma and lower pharynx of a wearer fitted with a device according to the present invention.
Figure 9:
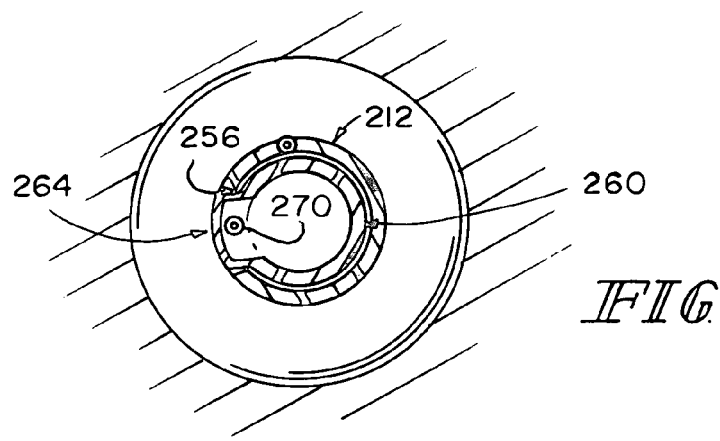
FIG. 9 illustrates a fragmentary sectional view taken generally along section lines 9-9 of FIG. 8; and, FIGS. 10-13 illustrate several views of an alternative detail to a detail illustrated in FIGS. 5-6, with FIGS. 10-11 illustrating perspective views of the illustrated detail in disassembled (FIG. 10) and assembled (FIG. 11) configurations, respectively, and FIGS. 12-13 illustrating sectional views taken generally along section lines 12, 13-12, 13 of FIG. 11 in assembled (FIG. 12) and partially disassembled (FIG. 13) configurations.
Figure 12:
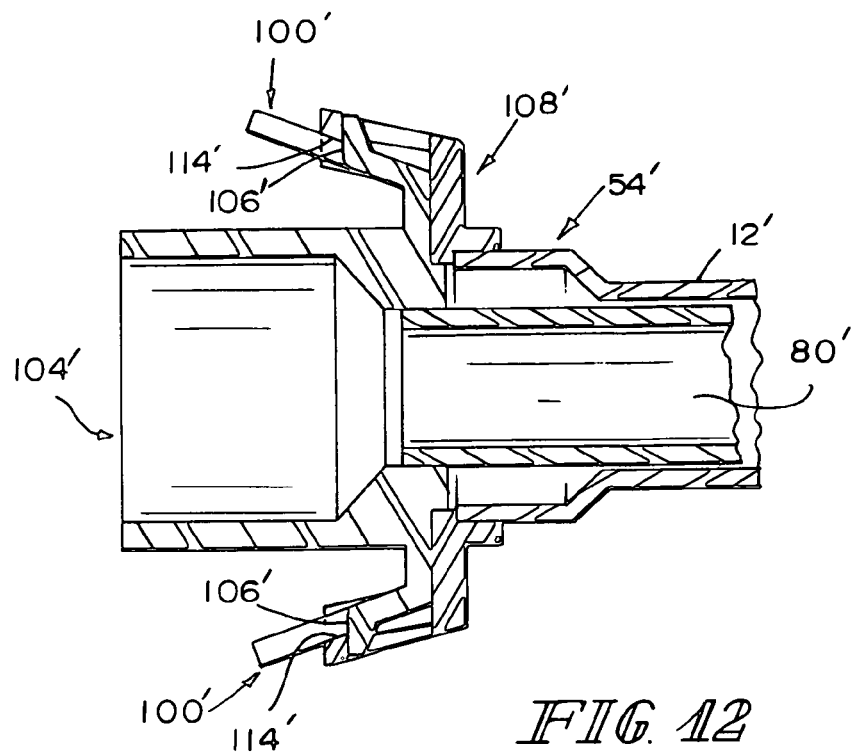
Figure 13:
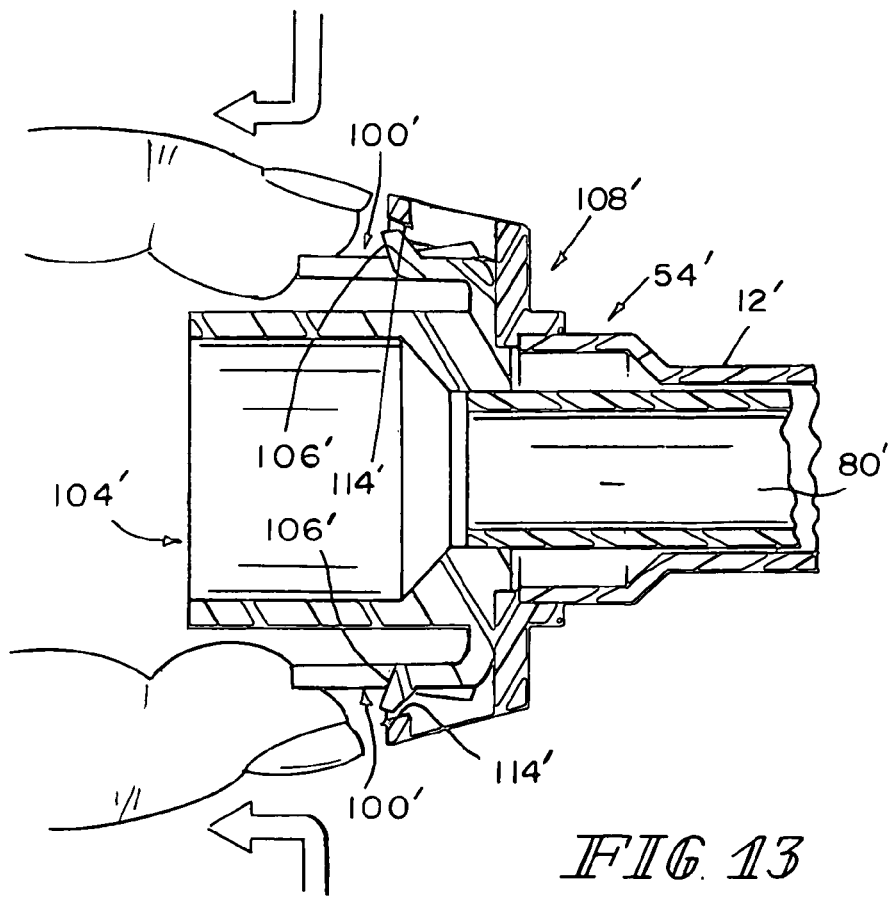

Referring now to FIGS. 7-9, in a second embodiment of the tracheotomy tube apparatus, the fenestration 256 and the raised region 264, FIGS. 8-9, are on the anterior aspects of outer cannula 212 and inner cannula 260, respectively, rather than on the posterior aspects, as was the case with the embodiment illustrated in FIGS. 1-6. This also requires that the open end 272 of suction tube 270 be on the anterior aspect, since open end 272 is oriented at the bottom of the fenestration 256 and the fenestration 256 is on the anterior aspect of the outer cannula 212 in this embodiment. Also, again since the fenestration 256 is on the anterior aspect of the outer cannula 212, the resilient, balloon-like region 282, FIG. 7, and region 286 between region 282 and valve 288 of speaking inner cannula 280 are all on the anterior aspect of inner cannula 280. Since the wearer 220 may spend at least a considerable portion of his or her time in a supine orientation, this embodiment places the fenestration 256 on the upper side of the outer cannula 212 where it is somewhat less susceptible to pooling and leakage of secretions 232 through the fenestration 256.

What is claimed is:

1. A tracheotomy tube apparatus including an outer cannula having first and second ends, a fenestration along the length of the outer cannula between the first and second ends, a first inner cannula sized for insertion into the outer cannula, the first inner cannula including a flexible, balloon-like region which lies adjacent the fenestration when the first inner cannula is properly oriented within the outer cannula, the first inner cannula further including a valve adjacent the distal end of the first inner cannula, the first inner cannula further including a region between the flexible, balloon-like region and the valve which provides a passageway between the first inner cannula and the outer cannula when the first inner cannula is properly oriented within the outer cannula.

2. The apparatus of claim 1 including at least one tab provided on an outer end of one of the outer cannula and the inner cannula, the at least one tab including an engaging surface, at least one coupler provided on an outer end of the other one of the outer cannula and the inner cannula for engagement by the at least one tab, the at least one coupler including a portion for cooperating with the engaging surface and a notch for receiving a portion of the at least one tab for orienting the inner cannula in a predetermined orientation with respect to the outer cannula.

3. The apparatus of claim 2 wherein the at least one tab is flexibly formed or mounted to said one of the outer cannula and the inner cannula.

4. The apparatus of claim 1 wherein the outer cannula further comprises an inflatable cuff formed by a sleeve including a first end, a second end, and a third region between the first and second ends, the sleeve located around the outer cannula with at least the first end of the sleeve between the outer cannula and the third region of the sleeve, and a first conduit extending from a first end of the outer cannula to the cuff for introducing an inflating fluid into the cuff when it is desired to inflate the cuff and removing inflating fluid from the cuff when it is desired to deflate the cuff.

5. The apparatus of claim 4 including at least one tab provided on an outer end of one of the outer cannula and the inner cannula, the at least one tab including an engaging surface, at least one coupler provided on an outer end of the other one of the outer cannula and the inner cannula for engagement by the at least one tab, the at least one coupler including a portion for cooperating with the engaging surface and a notch for receiving a portion of the at least one tab for orienting the inner cannula in a predetermined orientation with respect to the outer cannula.

6. The apparatus of claim 4 wherein the first end of the sleeve and the second end of the sleeve are both between the outer cannula and the third region of the sleeve.

7. The apparatus of claim 6 including at least one tab provided on an outer end of one of the outer cannula and the inner cannula, the at least one tab including an engaging surface, at least one coupler provided on an outer end of the other one of the outer cannula and the inner cannula for engagement by the at least one tab, the at least one coupler including a portion for cooperating with the engaging surface and a notch for receiving a portion of the at least one tab for orienting the inner cannula in a predetermined orientation with respect to the outer cannula.

8. The apparatus of claim 6 further comprising a second inner cannula for placement in the outer cannula when the first inner cannula is removed therefrom, the second inner cannula comprising a second conduit to evacuate a region of the trachea of the wearer adjacent the cuff, the second conduit including an opening which lies adjacent the closest point in the fenestration to the cuff when the second inner cannula is in a use orientation in the outer cannula.

9. The apparatus of claim 8 including at least one tab provided on an outer end of one of the outer cannula and the inner cannula, the at least one tab including an engaging surface, at least one coupler provided on an outer end of the other one of the outer cannula and the inner cannula for engagement by the at least one tab, the at least one coupler including a portion for cooperating with the engaging surface and a notch for receiving a portion of the at least one tab for orienting the inner cannula in a predetermined orientation with respect to the outer cannula.

10. The apparatus of claim 8 further comprising a first coupler provided on an outer end of the outer cannula, a second coupler provided on an outer end of the first inner cannula, one of the first and second couplers provided with at least one surface for guiding the first inner cannula into a predetermined orientation with respect to the outer cannula when the first inner cannula is inserted into the outer cannula, the other of the first and second couplers provided with a cooperating surface for cooperating with the at least one surface for guiding the first inner cannula into the predetermined orientation with respect to the outer cannula.

11. The apparatus of claim 10 further comprising a first coupler provided on an outer end of the outer cannula, a second coupler provided on an outer end of the second inner cannula, one of the first and second couplers provided with at least one surface for guiding the second inner cannula into a predetermined orientation with respect to the outer cannula when the second inner cannula is inserted into the outer cannula, the other of the first and second couplers provided with a cooperating surface for cooperating with the at least one surface for guiding the second inner cannula into the predetermined orientation with respect to the outer cannula.

12. The apparatus of claim 8 further comprising a first coupler provided on an outer end of the outer cannula, a second coupler provided on an outer end of the second inner cannula, one of the first and second couplers provided with at least one surface for guiding the second inner cannula into a predetermined orientation with respect to the outer cannula when the second inner cannula is inserted into the outer cannula, the other of the first and second couplers provided with a cooperating surface for cooperating with the at least one surface for guiding the second inner cannula into the predetermined orientation with respect to the outer cannula.

13. The apparatus of claim 6 further comprising a first coupler provided on an outer end of the outer cannula, a second coupler provided on an outer end of the first inner cannula, one of the first and second couplers provided with at least one surface for guiding the first inner cannula into a predetermined orientation with respect to the outer cannula when the first inner cannula is inserted into the outer cannula, the other of the first and second couplers provided with a cooperating surface for cooperating with the at least one surface for guiding the first inner cannula into the predetermined orientation with respect to the outer cannula.

14. The apparatus of claim 6 further comprising a first coupler provided on an outer end of the outer cannula, a second coupler provided on an outer end of a second inner cannula, one of the first and second couplers provided with at least one surface for guiding the second inner cannula into a predetermined orientation with respect to the outer cannula when the second inner cannula is inserted into the outer cannula, the other of the first and second couplers provided with a cooperating surface for cooperating with the at least one surface for guiding the second inner cannula into the predetermined orientation with respect to the outer cannula.

15. The apparatus of claim 4 further comprising a second inner cannula for placement in the outer cannula when the first inner cannula is removed therefrom, the second inner cannula comprising a second conduit to evacuate a region of the trachea of the wearer adjacent the cuff, the second conduit including an opening which lies adjacent the closest point in the fenestration to the cuff when the second inner cannula is in a use orientation in the outer cannula.

16. The apparatus of claim 4 further comprising a first coupler provided on an outer end of the outer cannula, a second coupler provided on an outer end of the first inner cannula, one of the first and second couplers provided with at least one surface for guiding the first inner cannula into a predetermined orientation with respect to the outer cannula when the first inner cannula is inserted into the outer cannula, the other of the first and second couplers provided with a cooperating surface for cooperating with the at least one surface for guiding the first inner cannula into the predetermined orientation with respect to the outer cannula.

17. The apparatus of claim 4 further comprising a first coupler provided on an outer end of the outer cannula, a second coupler provided on an outer end of a second inner cannula, one of the first and second couplers provided with at least one surface for guiding the second inner cannula into a predetermined orientation with respect to the outer cannula when the second inner cannula is inserted into the outer cannula, the other of the first and second couplers provided with a cooperating surface for cooperating with the at least one surface for guiding the second inner cannula into the predetermined orientation with respect to the outer cannula.

18. The apparatus of claim 4 wherein the first end of the sleeve and the second end of the sleeve are both between the outer cannula and the third region of the sleeve.

19. The apparatus of claim 1 further comprising a second inner cannula for placement in the outer cannula when the first inner cannula is removed therefrom, the second inner cannula comprising a second conduit to evacuate a region of the trachea of the wearer adjacent the cuff, the second conduit including an opening which lies adjacent the closest point in the fenestration to the cuff when the second inner cannula is in a use orientation in the outer cannula.

20. The apparatus of claim 1 further comprising a first coupler provided on an outer end of the outer cannula, a second coupler provided on an outer end of the first inner cannula, one of the first and second couplers provided with at least one surface for guiding the first inner cannula into a predetermined orientation with respect to the outer cannula when the first inner cannula is inserted into the outer cannula, the other of the first and second couplers provided with a cooperating surface for cooperating with the at least one surface for guiding the first inner cannula into the predetermined orientation with respect to the outer cannula.

21. The apparatus of claim 1 further comprising a first coupler provided on an outer end of the outer cannula, a second coupler provided on an outer end of a second inner cannula, one of the first and second couplers provided with at least one surface for guiding the second inner cannula into a predetermined orientation with respect to the outer cannula when the second inner cannula is inserted into the outer cannula, the other of the first and second couplers provided with a cooperating surface for cooperating with the at least one surface for guiding the second inner cannula into the predetermined orientation with respect to the outer cannula.

* * * * *